(12) United States Patent
Briggs

(10) Patent No.: US 11,160,440 B2
(45) Date of Patent: Nov. 2, 2021

(54) ENDOSCOPE SYSTEM AND A WATER BOTTLE CAP ASSEMBLY FOR SUCH AN ENDOSCOPE SYSTEM

(71) Applicant: STARMEDUK LIMITED, Northamptonshire (GB)

(72) Inventor: Justin J. Briggs, Northampton (GB)

(73) Assignee: STARMEDUK LIMITED, Northamptonshire (GB)

( * ) Notice: Subject to any disclaimer, the term of this patent is extended or adjusted under 35 U.S.C. 154(b) by 380 days.

(21) Appl. No.: 16/088,499

(22) PCT Filed: Feb. 10, 2017

(86) PCT No.: PCT/GB2017/050363
§ 371 (c)(1),
(2) Date: Sep. 26, 2018

(87) PCT Pub. No.: WO2017/168117
PCT Pub. Date: Oct. 5, 2017

(65) Prior Publication Data
US 2019/0117046 A1 Apr. 25, 2019

(30) Foreign Application Priority Data
Mar. 30, 2016 (GB) .................................. 1605295

(51) Int. Cl.
*A61B 1/00* (2006.01)
*A61B 1/015* (2006.01)
(Continued)

(52) U.S. Cl.
CPC ...... *A61B 1/00119* (2013.01); *A61B 1/00128* (2013.01); *A61B 1/015* (2013.01); *A61B 1/126* (2013.01); *A45F 2003/163* (2013.01)

(58) Field of Classification Search
CPC .......... A61M 1/00119; A61M 1/00128; A61M 1/00137; A61M 1/015; A61M 1/0126; (Continued)

(56) References Cited

U.S. PATENT DOCUMENTS 5,041,106 A * 8/1991 Noji ...................... A61M 5/162
604/411
5,188,628 A 2/1993 Rani et al.
(Continued)

FOREIGN PATENT DOCUMENTS

GB 2063836 A 6/1981

OTHER PUBLICATIONS

International Search Report dated May 17, 2017 for PCT Patent Application No. PCT/GB2017/050363, 12 pages.

*Primary Examiner* — Aaron B Fairchild
(74) *Attorney, Agent, or Firm* — Smith IP Services, P.C.

(57) ABSTRACT

An endoscope system and particularly but not exclusively a water bottle cap assembly for an endoscope/endoscopic device. An endoscope system includes an endoscope device and means for directing a fluid adjacent a tip of the endoscope device. The fluid directing means includes a fluid container for containing the fluid, the container including an inlet and an outlet. The system further includes separating means for separating liquid or solid particles from gas entering the container through the inlet.

21 Claims, 11 Drawing Sheets

(51) Int. Cl.
*A61B 1/12* (2006.01)
*A45F 3/16* (2006.01)

(58) Field of Classification Search
CPC .... A61M 1/00131; A61M 1/12; A61M 1/126; A61M 1/127; A61M 1/0058; A61M 3/00; A61M 3/02; A61B 2218/002
See application file for complete search history.

(56) References Cited

U.S. PATENT DOCUMENTS

| | | | |
|---|---|---|---|
| 6,485,412 B1 | 11/2002 | Byrne | |
| 2009/0101562 A1 | 4/2009 | Newton | |
| 2012/0091092 A1 | 4/2012 | Adams et al. | |
| 2012/0095293 A1* | 4/2012 | Bendele | A61B 1/00137 600/158 |
| 2012/0095391 A1* | 4/2012 | Bendele | A61B 1/00128 604/26 |
| 2015/0297063 A1* | 10/2015 | Wolcott | A61B 1/00068 600/158 |

* cited by examiner

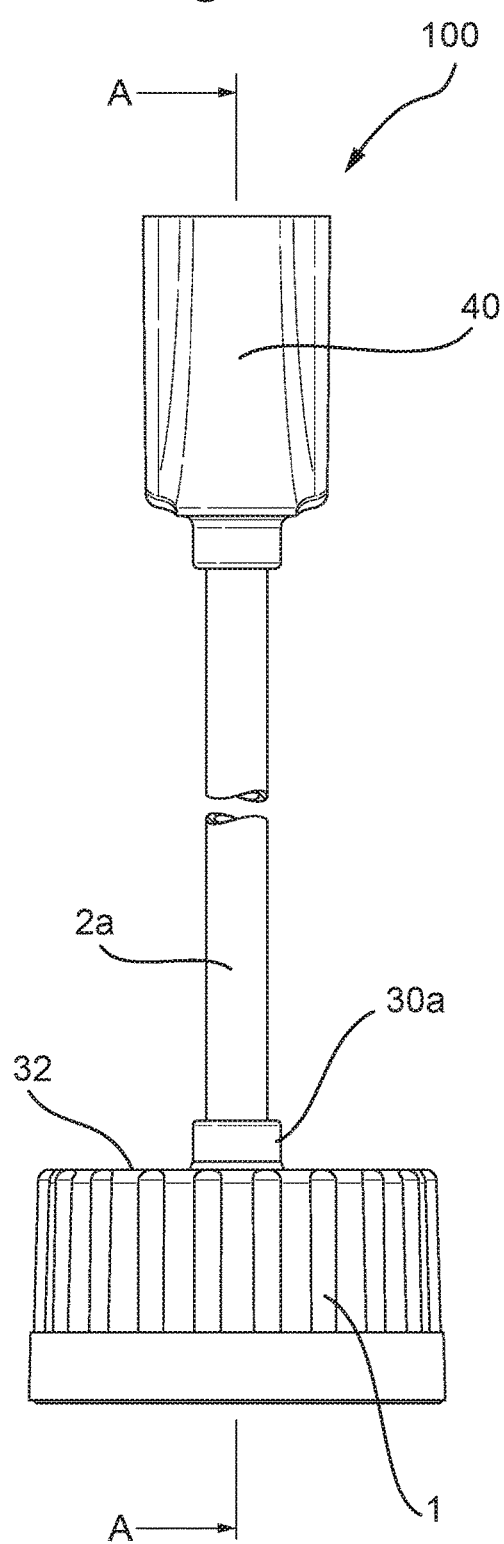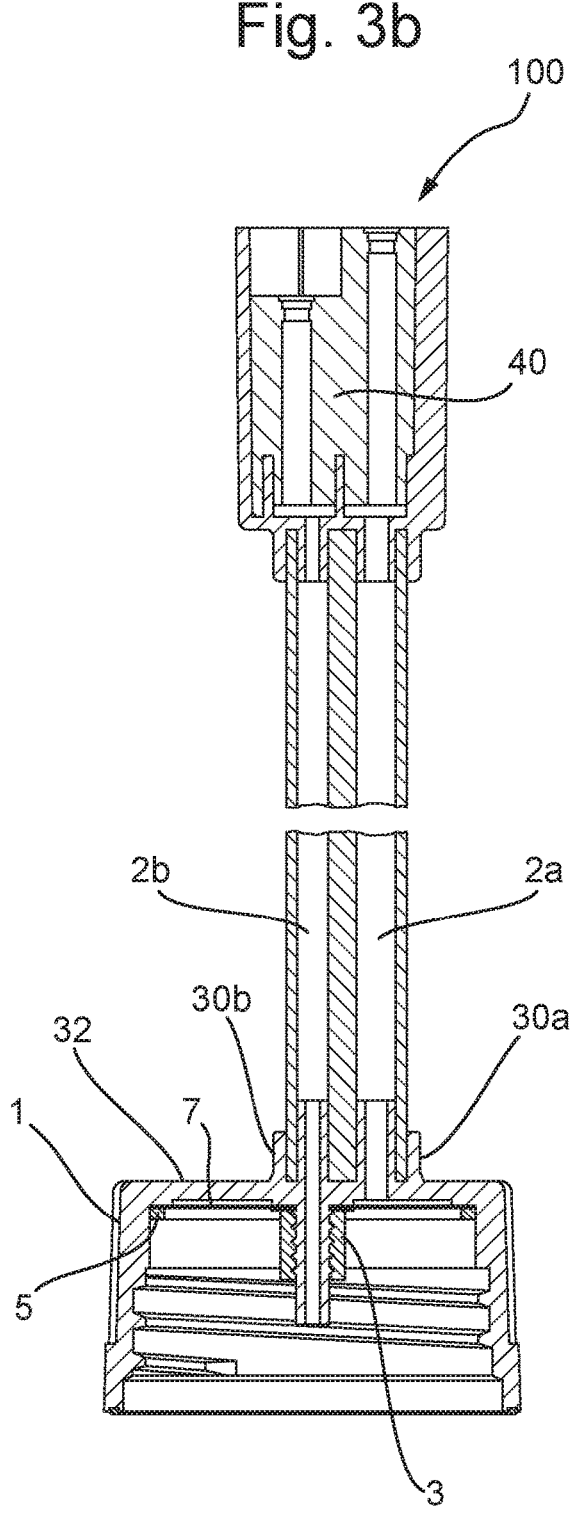

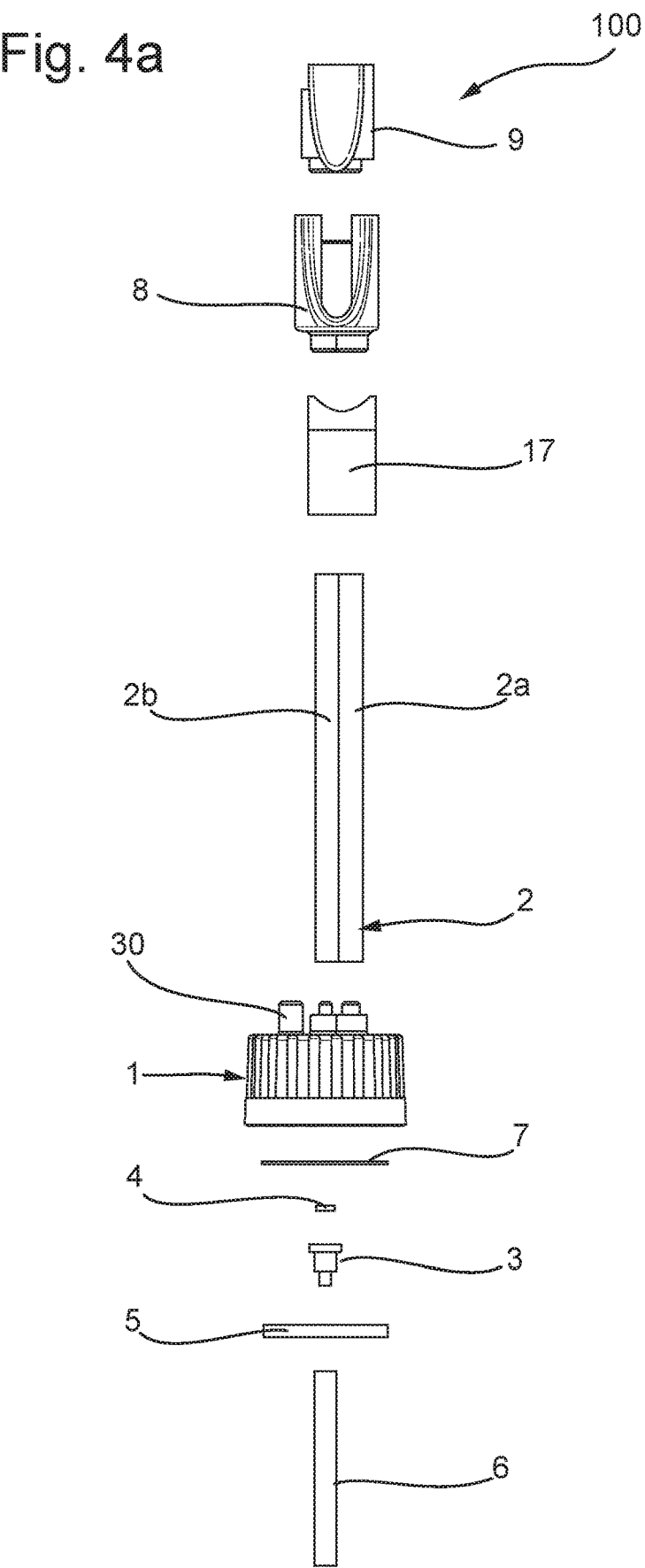

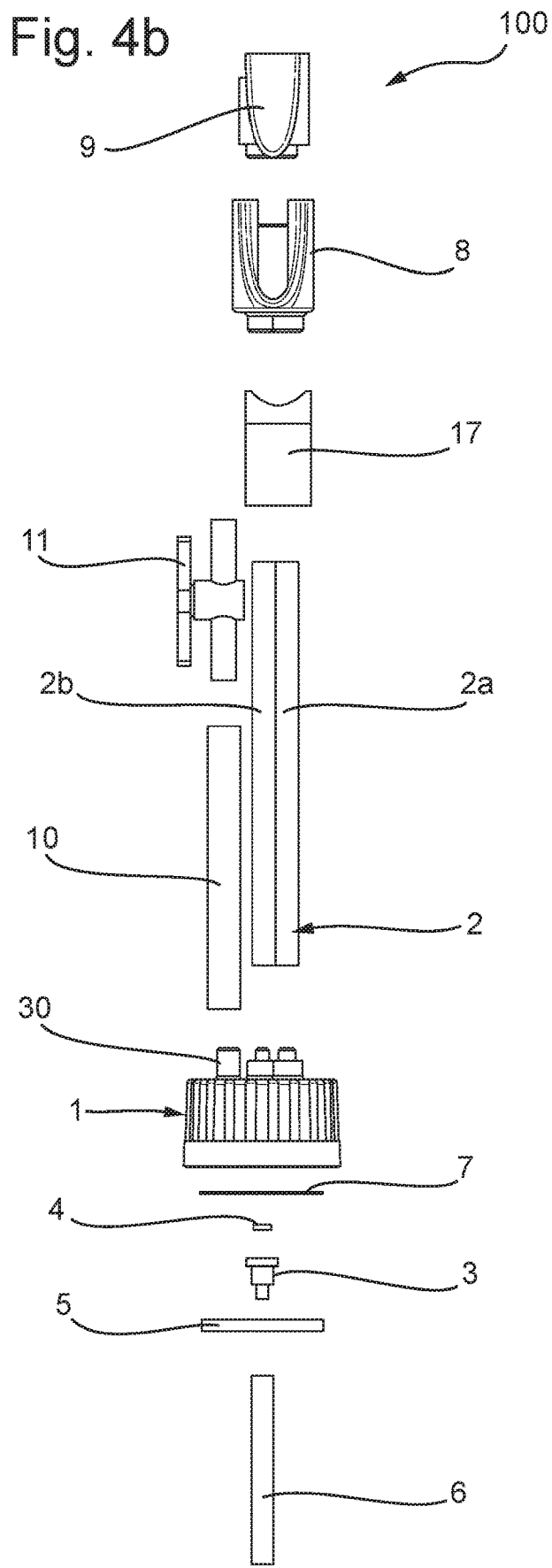

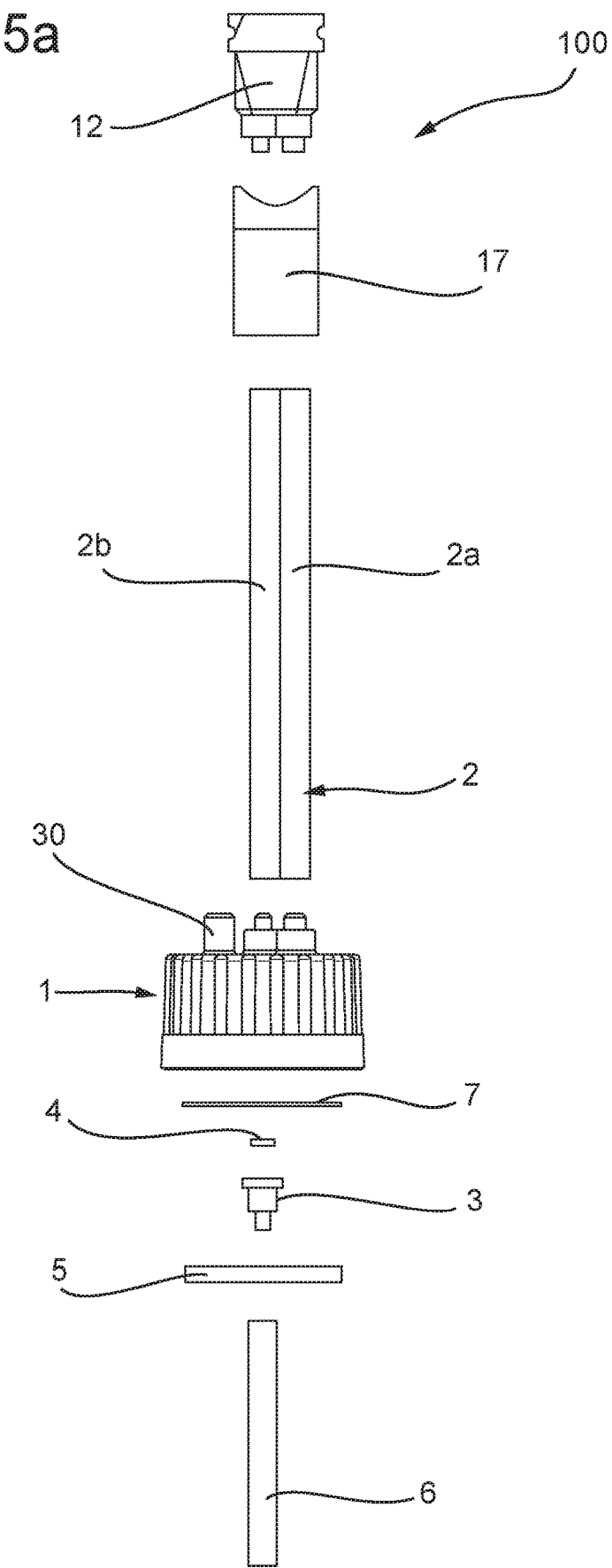

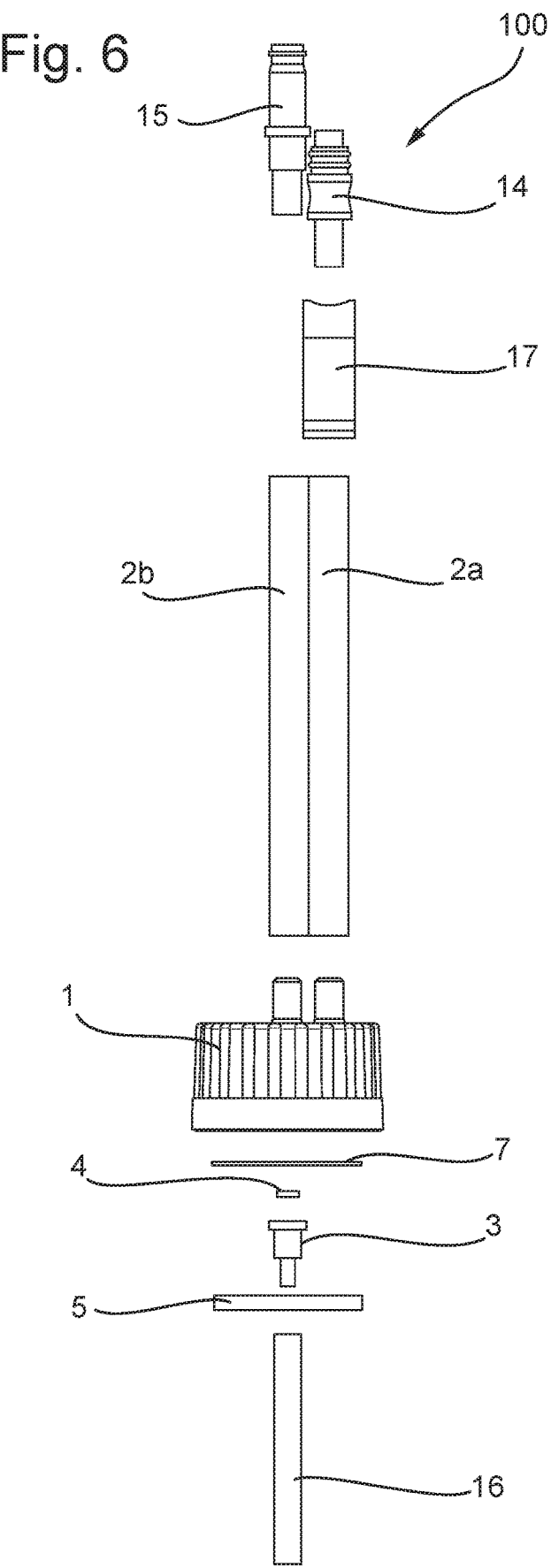

ENDOSCOPE SYSTEM AND A WATER BOTTLE CAP ASSEMBLY FOR SUCH AN ENDOSCOPE SYSTEM

CROSS-REFERENCE TO RELATED APPLICATIONS

This application is a national stage under 35 USC 371 of International Application No. PCT/GB2017/050363 filed on 10 Feb. 2017, which claims the benefit of the filing date of GB Application No. 1605295.3 filed on 30 Mar. 2016. The entire disclosures of these prior applications are incorporated herein by this reference.

The present invention relates to an endoscope system and particularly but not exclusively to a water bottle cap assembly for an endoscope/endoscopic device.

BACKGROUND OF THE INVENTION

There are various types of flexible endoscope systems known in the endoscopy industry (e.g., Olympus®, Fuji®, Pentax® endoscope systems), and the present invention is of particular relevance to what is commonly referred to as a water bottle cap assembly for an endoscope system.

Typically, a flexible endoscope system may be used in surgery or general investigative work and may comprise a control head and a flexible tubing system with a maneuverable tip. In common designs, the control head is connected to a light source system via an 'umbilical' cord, through which pass other tubes conveying for example air, water and suction. An endoscope system can also comprise other components such as: means for capturing and transmitting images to a viewer including for example a camera lens system; means for directing a fluid adjacent a camera and/or lighting lens system to assist viewing and/or to effectuate irrigation during the procedure; and means to allow entry of medical instruments and/or manipulators.

In use, an endoscope system normally requires a water source/bottle which is used as a container of a liquid, typically water, for cleaning the maneuverable tip (which may be provided with one or more lenses associated with a camera and/or lighting) and/or for insufflating. Typically, an endoscope system comprises an air pump which draws ambient air from the surrounding environment (e.g. the procedure room). The air is used to pressurise the water bottle and force the water from the bottle. The water is allowed to be released from the water bottle under the force of the air by way of an air water button (which operates a valve). In this way, water from the water bottle may be selectively provided across the tip of the endoscope so as to clean the tip, specifically the camera/light lenses.

A problem associated with known endoscope systems is that the incoming ambient air flowing from the surrounding environment and directly into the water bottle may convey contaminants into the water bottle. The water which is held by the water bottle and to be conveyed to the maneuverable tip is thereby exposed to contaminants. This can be undesirable, particular where an endoscope device is to be used in surgical procedures.

Thus, it is an object of the present invention to provide an endoscope system and/or a water bottle cap assembly which addresses some of the problems associated with known endoscope systems.

STATEMENT OF INVENTION

In a first aspect, the present invention provides an endoscope system comprising an endoscope device and means for directing a fluid adjacent a tip of the endoscope device, wherein said fluid directing means comprises a fluid container for containing said fluid, the container comprising an inlet and an outlet, and characterised in that the system further comprises separating means for separating liquid or solid particles from gas entering the container through said inlet.

The container may comprise said separating means. Preferably, said separating means is positioned in a chamber of the container in which chamber said fluid is held. More preferably, said separating means is positioned adjacent the inlet. Said separating means may positioned spaced from the inlet, the cross-sectional area of the fluid flow path between the inlet and said separating means increasing in the direction of fluid flow from the inlet to said separating means. It should be noted that the fluid flow path may be a gas flow path, for example an air flow path and/or a carbon dioxide flow path (and/or a flow path for any other suitable gas).

The outlet preferably comprises a fluid conduit which may extend through said separating means from the interior of the fluid container to the exterior of the fluid container.

The endoscope system preferably comprises securing means for securing said separating means in position, the securing means being releasably attached to the fluid conduit of the outlet. The securing means may be releasably attached to the fluid conduit by means of a screw thread provided on the securing means and fluid conduit. The securing means may press said separating means against the container so as to clamp said separating means in position. The securing means may be releasably attached to the fluid conduit by means of a push/interference fit or a snap-clip fit. Said push/interference fit may attach the securing means to the fluid conduit so that the securing means presses said separating means against the container so as to clamp said separating means in position. The securing means may be concentrically arranged with the fluid conduit of the outlet.

The endoscope system may comprise a sealing member preferably located between said separating means and the securing means and/or the container.

The container may yet further comprise an opening and a closure member for closing the opening. Preferably, the closure member comprises said inlet and outlet of the container.

The endoscope system may comprise a perimeter sealing member located between the perimeter of the opening and the closure member, the opening and closure member clamping said sealing member and said separating means together. Preferably, the closure member selectively closes the opening by means of a screw thread provided on the closure member and about the opening.

The endoscope system may comprise an inner sealing member located between the separating means and the securing means and/or the container. The inner sealing member and the perimeter sealing member may be integral with one another as a one-piece element. The inner sealing member may be located radially inwardly relative to the perimeter sealing member, the inner sealing member and the perimeter sealing member being connected to one another by at least one radially extending spoke. The inner sealing member and the perimeter sealing member may be connected to one another by a plurality radially extending spokes circumferentially spaced equidistant from each other. The inner sealing member and the perimeter sealing member may be connected to one another by three radially extending spokes circumferentially spaced equidistant from each other. The, or each, spoke may abut the separating means so as to provide support thereto. The, or each, spoke may be resiliently sprung biased towards the separating means so as to press against the separating means. The inner sealing member may abut a radially inner annular region of the separating means and the perimeter sealing member may abut a radially outer annular region of the separating means, to thereby retain the separating means in position.

Said separating means may comprise a filter medium. Preferably, the filter medium comprises a 0.2 micron filter membrane. More preferably, the filter medium has an annular shape. Said separating means may be located in a fluid pathway connected to said inlet.

The endoscope system may comprise a frangible line in the container, wherein the frangible line is preferably a closed loop such that when the frangible line is selectively broken in use, a portion of the container within said closed loop may be removable to provide an auxiliary port between the interior and exterior of the container. Preferably, the frangible line is located on the container adjacent said inlet so that gas, entering the container through the said auxiliary port, flows through said separating means.

In a second aspect, the present invention provides an endoscope water bottle cap for an endoscopic device comprising: an inlet through which, in use, a gas flows into a water bottle associated with the cap; an outlet through which, in use, water flows out of the water bottle to the endoscopic device; characterised in that the water bottle cap further comprises separating means arranged to separate liquid or solid particles from the gas entering the water bottle.

The separating means may have an annular shape. The separating means may be located adjacent an upper wall of the water bottle cap. The separating means may be arranged on an internal surface of the upper wall of the water bottle cap. The separating means may be retained on an internal surface of the upper wall of the water bottle cap by securing means.

The securing means may comprise a sealing member. The sealing member may comprise an inner sealing member and a perimeter sealing member. The inner sealing member is discrete from the perimeter sealing member. The inner sealing member and the perimeter sealing member may be separately assembled in the cap. The inner sealing member and the perimeter sealing member may be connected to one another by at least one readily extending spoke, to integrally form a one-piece single sealing member. The inner sealing member and the perimeter sealing member may be connected to one another by a plurality radially extending spokes circumferentially spaced equidistant from each other. The or each spoke may abut the separating means so as to provide support thereto. The or each spoke may be resiliently sprung biased towards the separating means so as to press against the separating means. The inner sealing member may abut a radially inner annular region of the separating means and the perimeter sealing member may abut a radially outer annular region of the separating means, to thereby retain the separating means in position. The sealing member may be made of a resiliently deformable material.

The securing means may comprise a connector which may be secured to the internal surface of the upper wall of the water bottle cap by screw thread means, and/or push/interference fit means, and/or snap-fit means. Preferably the separating means is arranged between the first upper wall of the water bottle cap and the securing means. The separating means may be arranged between the inlet and the securing means.

Preferably, the cap further comprises a cavity that is provided between the upper wall of the water bottle cap and the separating means, and wherein the inlet opens in to said cavity.

The cap further may comprise a conduit in which said outlet is provided, the conduit extending through the separating means, from one side of the separating means to the other.

The separating means may be a filter, preferably made of porous material and/or of a deformable material.

The endoscope system and the water bottle cap assembly for such an endoscope system described herein, may allow a gas (e.g., air or $CO_2$) to be filtered before exposure to water in the water bottle so as to prevent contaminants from entering the water bottle during operation. Such a one-piece seal element allows for an easy and efficient assembly (or disassembly) of the securing means and hence of the separating means. Push/interference fit and/or snap-fir securing means also allows the sealing member, and hence the separating means, to be easily and efficiently secured and/or removed. Moreover, given separating means are enclosed and safely located in the endoscopic system and/or cap, no additional enclosures are needed to protect the separating means. The present invention is thus more easily manufactured, robust and cost-effective than conventional prior art apparatus. In addition, the present invention will have the advantage of being re-usable with minimal risk of cross contamination.

The endoscope system and the water bottle cap assembly could achieve such a separating process by providing separating means which could be placed in, on, or adjacent a wall of the cap. It will be also appreciated that the separating means could be placed at any locations along an input line, preferably an air input line, which is in fluid communication with the cap. Preferably, the separating means is located in a fluid pathway connected to the inlet so as to allow room air to be filtered before entering the water and/or container or water bottle.

It will be understood by the skilled person that these preferable and advantageous features may be combined with one another and that any resulting embodiments will also be embodiments of the invention.

DETAILED DESCRIPTION

A better understanding of the present invention will be obtained from the following detailed description. Embodiments of the present invention will now be described by way of example only with reference to the accompanying drawings, in which:

FIG. 1b is a second perspective view of the water bottle cap assembly shown in FIG. 1a;

FIG. 2a is a first perspective view of a water bottle cap of the assembly shown in FIG. 1a;

FIG. 2b is a second perspective view of a water bottle cap of the assembly shown in FIG. 1a;

FIG. 3a is a side view of the assembly shown in FIG. 1a;

FIG. 3b is a cross-sectional side view of the assembly shown in FIG. 1a;

FIG. 4a is an exploded side view of a water bottle cap assembly of a second embodiment of the present invention comprising an Olympus® endoscope connector system;

FIG. 4b is an exploded side view of a water bottle cap assembly of a third embodiment of the present invention comprising an Olympus® endoscope connector system and an incoming gas (carbon dioxide, $CO_2$) supply;

FIG. 5a is an exploded side view of a water bottle cap assembly of a fourth embodiment of the present invention comprising a Fuji® endoscope connector system;

FIG. 6 is an exploded side view of a water bottle cap assembly of a sixth embodiment of the present invention comprising a Pentax® endoscope connector system;

Embodiments of the present invention provide water bottle cap assemblies for use in endoscopy procedure. A water bottle cap assembly could be used for instrument cleaning and/or supporting irrigations. A water bottle cap assembly can be used with a variety of different water sources and in some cases can allow for provision of a secondary incoming gas supply such as carbon dioxide ($CO_2$).

Figure 1A:
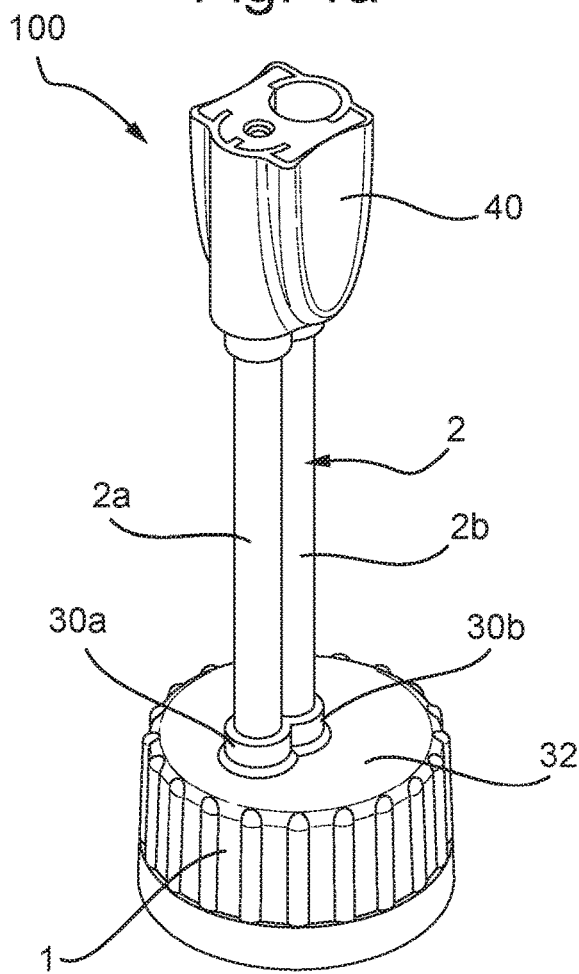
FIG. 1a is a first perspective view of a water bottle cap assembly of a first embodiment of the present invention.
Figure 1B:
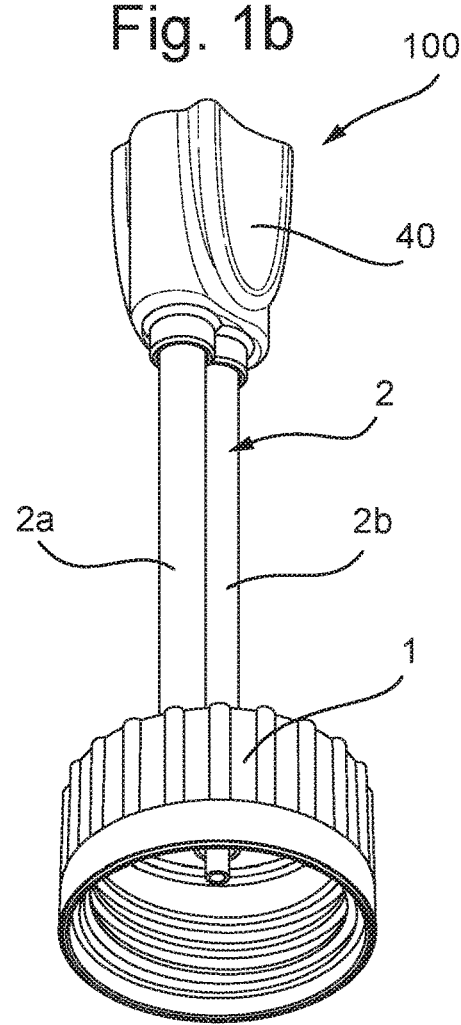

FIG. 1a and FIG. 1b show two different perspective views of a first water bottle cap assembly 100. The water bottle cap assembly 100 comprises a closure member such as a cap 1 for closing an opening in a bottle/container for holding water. The bottle/container provides a source of water during an endoscopy procedure. The cap 1 is configured (by way of screw threads) to engage a water bottle/container (not shown in the figures) and be secured thereto, and to engage with an endoscopic device (not shown in the figures) via a connector/adaptor 40. In an embodiment of the present invention, the cap 1 is connected to the endoscopic connector/adaptor 40 by means of a tubing arrangement 2 comprising a first tubular member 2a and a second tubular member 2b. The first tubular member 2a conveys air whilst the second tubular member 2b conveys water. In an embodiment of the present invention the tubing arrangement 2 comprises twin tubular members made of flexible material, and more preferably of a PVC material. It will be appreciated that the water bottle may be disposable, and that the bottle could contain liquids other than water. It will be also appreciated that different types of adaptors could be used for different types of endoscopic devices (e.g., Olympus®, Fuji® or Pentax® endoscopic devices).

Figure 2A:
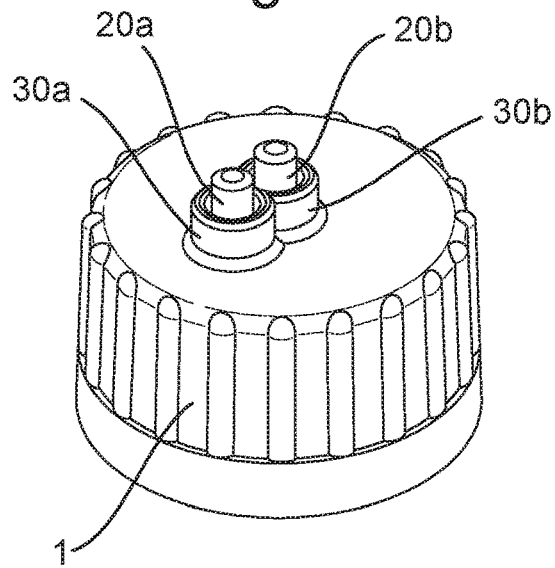
Figure 2B:
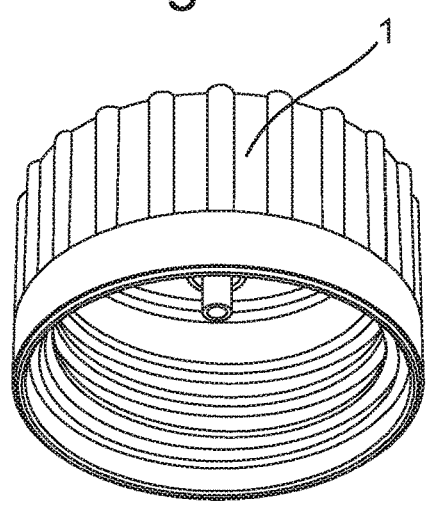

The cap 1 comprises a helical ridge or a thread running around the internal surface of a sidewall of the cap as shown in FIG. 1b and FIG. 2b. This allows the cap 1 to engage with the water bottle and be secured thereto. It will be appreciated that other securing means could be used to secure the cap 1 to the water bottle.

FIG. 2a shows a first perspective view of the water bottle cap 1 of the first embodiment shown in FIGS. 1a and 1b.

Figure 3C:
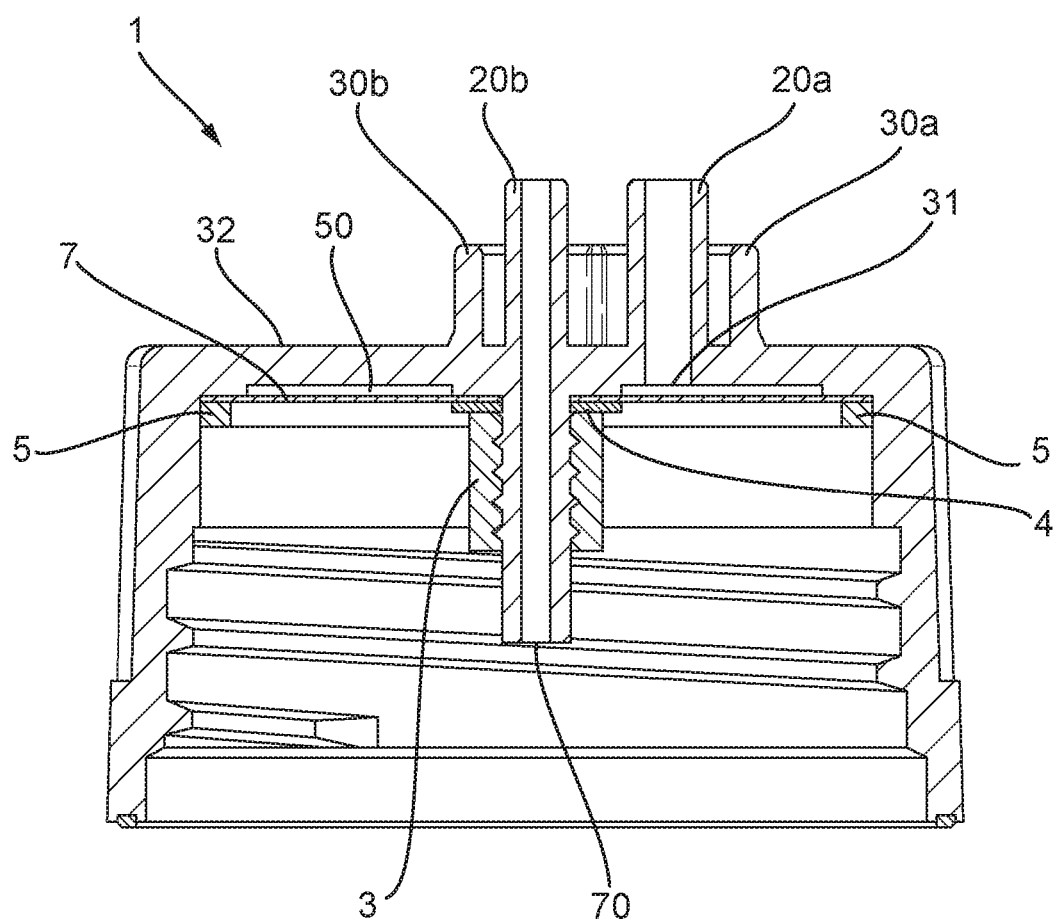
FIG. 3c is an enlarged cross-sectional side view of the cap shown in FIG. 3b.

FIG. 2b shows a second perspective view of the water bottle cap 1, and a cross-sectional view is shown in FIG. 3c. Further details of the water bottle cap assembly are shown in FIG. 3a and FIG. 3b.

The water bottle cap 1 shown in FIG. 1a and FIG. 2a comprises a first port 30a and a second port 30b protruding outwardly from the cap 1. The ports 30a and 30b extend outwardly from an external surface of a first upper wall 32 of the cap 1, as shown in FIG. 1a and FIG. 2a. The first port 30a includes a first inner conduit 20a extending outwardly from the external surface of the first upper wall 32 sufficiently enough to engage within an end of the first tubular member 2a by interference fit. Equally, the second port 30b may include a second inner conduit 20b extending outwardly from the external surface of the first upper wall 32 sufficiently enough to engage within an end of the second tubular member 2b by interference fit. It should be noted that other securing methods could be used. It will be appreciated that the water bottle cap assembly 100 could comprise different port(s) and/or tubing arrangement(s) (e.g., dual-lumen tubing).

In the first embodiment of the present invention, and as shown in FIG. 1b and FIG. 2b, the first port 30a is offset from the centre of the first upper wall 32 of the cap 1, whilst the second port 30b is located approximately in the centre of the first upper wall 32 (which is circular in shape). However, it will be appreciated that the ports 30a and 30b could be mutually arranged at any location on the cap 1.

As shown in FIG. 3b and FIG. 3c, the second inner conduit 20b extends inwardly from an internal surface of the first upper wall 32 sufficiently enough to engage a first water outlet tube 6 (shown in FIG. 4a) which, in the complete endoscope system, extends from the cap 1 into the water held in the water bottle. The first water outlet tube 6 engages the second inner conduit 20b and is retained in place by means of an interference fit. Alternatively, the outlet tube 6 may be retained in place by means of an interference fit with a connector 3, which is secured to the second inner conduit 20b by means of screw threads (it will be appreciated that alternative securing means could be used). As described below, the connector 3 will be understood to have a primary function of retaining the central portion of separating means (a separator 7) in position (in particular, in abutment against the cap).

Water contained in the water bottle is allowed to exit the water bottle, via the tube 6, through an outlet 70 (shown in FIG. 3c) which is provided in second inner conduit 20b. The water then flows to an endoscopic device through the second inner conduit 20b and via the second tubular member 2b.

The cap 1 further comprises a separator 7 which abuts the inner surface of the wall 32 of the cap 1. The separator 7 allows liquid or solid particles to be separated from the incoming air entering the water bottle through an inlet 31 of the first inner conduit 20a. As mentioned above, it should be noted that an endoscope system typically comprises an air pump which draws air from the surrounding environment i.e. the procedure room. As the room air is conveyed into the water bottle, the separator 7 separates and removes any liquid or solid particulates in the air. This process allows the incoming room air, which will be then used to pressurise the water bottle, to be sterilized. The water could be then released from the water bottle by an air water button (not shown) across a camera/lighting lens to assist viewing during the procedure. It will be appreciated that the air pump may be also used to insufflate during the procedure.

The skilled person will understand that the separator 7 can be a filter, preferably made of a porous material, and more preferably but not-exclusively of a resiliently deformable material. In the embodiments of the present invention shown in the accompanying drawings, the separator 7 is a membrane made of a 0.2 µm filter material. The membrane has an annular shape. It will be appreciated that different material porosity could be used.

It will be appreciated that the separator 7 could be placed in, on, or adjacent the first upper wall 32 of the cap 1. It will be also appreciated that the separator 7 could be placed at any locations along the tubing arrangements 2, in particular along the first tubular member 2a and upstream of the cap 1. It should be also noted that the separator 7 could either extend entirely on the inner surface of the wall 32, or partially in a region in proximity to the inlet 31.

The cap 1 further comprises a seal/gasket 5 which abuts the separator 7 as shown in FIG. 3c and FIG. 4a. The gasket 5 is held adjacent the inner surface of the cap wall 32 (with the separator 7 sandwiched therebetween) by means of an interference fit with the side walls of the cap. The separator 7 is arranged between the cap 1 and the gasket 5, and more specifically, between the gasket 5 and an annular perimeter portion of the inner surface of the upper wall 32 of the cap 1. It should be noted that the gasket 5 could be made of a resiliently deformable material, ideally having elastic properties. For example, the gasket could be a rubber O-ring seal. In use, when the cap 1 is screw threadedly engaged with the opening of the water bottle, the bottle opening abuts the seal/gasket 5 and presses/clamps the seal/gasket 5 against upper wall 32. In this way, the seal/gasket 5 provides support for the radially outermost perimeter of separator 7 and reduces the possibility of incoming air leaking past the separator 7 at said perimeter. The seal/gasket 5 also expands radially outwardly so as to press against the cap side walls, and this further reduces the possibility of incoming air leaking past the separator 7 at said perimeter.

The central part of the separator 7 is similarly held in place a second seal/gasket 4 which abuts the separator 7 as shown in FIG. 3c. The gasket 4 is held adjacent the inner surface of the cap wall 32 (with the separator 7 sandwiched therebetween) by means of an interference fit with the second inner conduit 20b. The separator 7 is arranged between the cap 1 and the gasket 4, and more specifically, between the gasket 4 and a second annular portion of the inner surface of the upper wall 32 of the cap 1. It should be noted that the gasket 4 could be made of a resiliently deformable material, ideally having elastic properties. For example, the gasket could be a rubber O-ring seal. In use, when the connector 3 is screw threadedly engaged the second inner conduit 20b, the connector 3 abuts the seal/gasket 4 and presses/clamps the seal/gasket 4 against upper wall 32. In this way, the seal/gasket 4 provides support for the radially innermost perimeter of separator 7 and reduces the possibility of incoming air leaking past the separator 7 at said perimeter. The seal/gasket 4 also expands radially inwardly so as to press against the second inner conduit 20b, and this further reduces the possibility of incoming air leaking past the separator 7 at said perimeter.

FIG. 3c also shows that the water bottle cap 1 further comprises a recess 50 in the inner surface of the first upper wall 32 of the cap. The recess 50 has an annular shape and is provided between the aforementioned first and second annular portions of said inner surface of the upper cap wall 32. The inlet 31 opens into the recess 50, and so incoming air flows from the first inner conduit 20a into a cavity defined by the recess 50, the aforementioned first and second annular portions, and the separator 7. The recess 50 effectively increases the cross-sectional area of the flow path of the incoming air (or gas) in the direction of flow. As a result, a reduction of mass flow rate of the incoming air, caused by the flow resistance of a separator, can be partially or wholly compensated for or mitigated.

It will be appreciated that different relative arrangements of filtering/separating means and securing/sealing means are also possible.

It will be also appreciated that the water bottle cap assembly 100 (or adapted versions thereof) can be arranged with different types of commercially available endoscopic devices (e.g., Olympus®, Fuji® or Pentax® endoscopic devices) as shown in FIGS. 4 to 6.

FIG. 4a shows an exploded view of a water bottle cap assembly 100 for an endoscopic device comprising an Olympus® endoscope connector system. The water bottle cap 1 comprises a third port 30 which extends outwardly from an external surface of the first upper wall 32 of the cap 1. FIG. 4b shows a first $CO_2$ tubular member 10 which engages the third port 30. An incoming secondary gas (carbon dioxide, $CO_2$) supply could be conveyed to the water bottle via the first $CO_2$ tubular member 10 and into the water bottle through the first port 30. The incoming flow is regulated by a valve 11. It should be noted that $CO_2$ is typically used in endoscopic procedures as it is more readily absorbed by the body.

In this version of the water bottle cap assembly, the connector 3 is provided with a boss at an end of the connector 3 distil to the seal/gasket 4 wherein the boss has an outer diameter sized to be received with an interference fit within an end of the outlet tube 6. The connector 3 then performs the dual functions of retaining a central portion of the separator 7 in position and also of receiving the water outlet tube 6.

In addition to the features already described, FIG. 4a and FIG. 4b also show an outer connector case 8, an inner connector seal 9, and a pinch clamp 17 for an Olympus® endoscopic device.

Figure 5B:
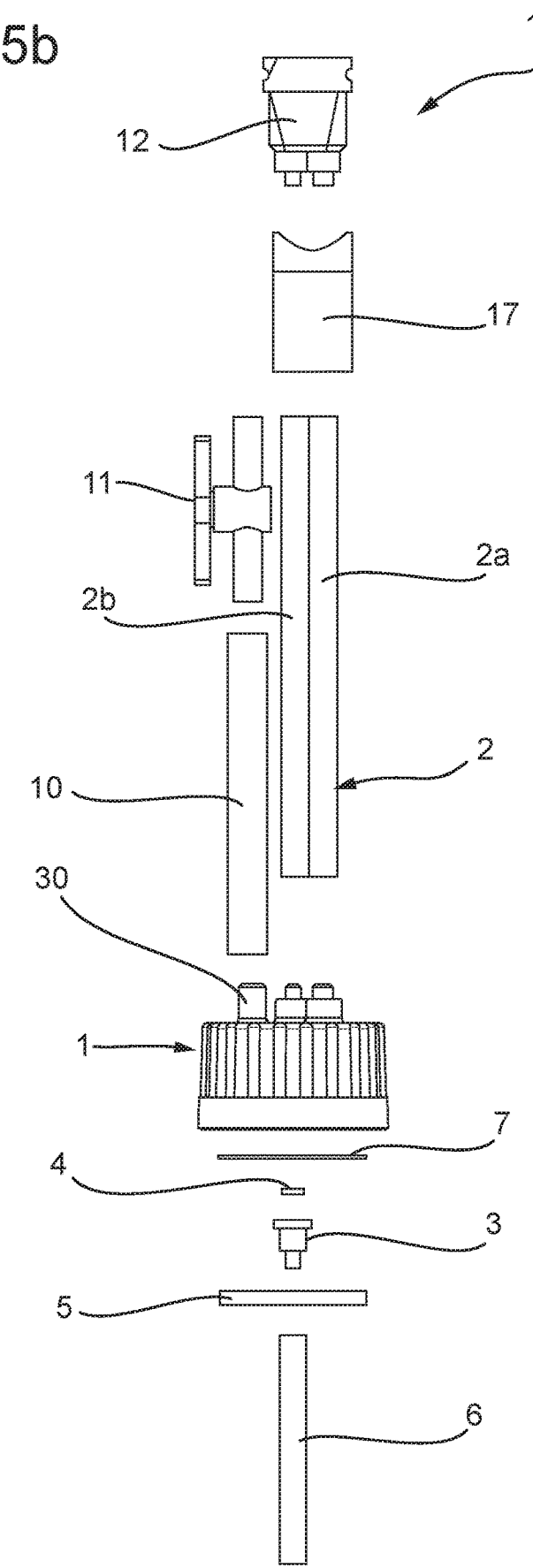
FIG. 5b is an exploded side view of a water bottle cap assembly of a fifth embodiment of the present invention comprising a Fuji® endoscope connector system and an incoming gas (carbon dioxide, $CO_2$) supply.

FIG. 5a and FIG. 5b show an exploded view of an embodiment of a water bottle cap assembly 100 for a Fuji® endoscope device. A connector 12 and a pinch clamp 17 for a Fuji® endoscopic device are shown.

FIG. 6 shows an exploded view of a water bottle cap assembly for an endoscopic device comprising a Pentax® endoscope connector system. Conversely to the embodiments discussed above, in the embodiment shown in FIG. 6, a water cap assembly 100 comprises a tubing arrangement 2 which includes a first tubular member 2a conveying air and water, and a second tubular member 2b conveying air only. FIG. 6 shows an air water connector 14 and a water connector 17 for a Pentax® endoscopic device.

Figure 7:
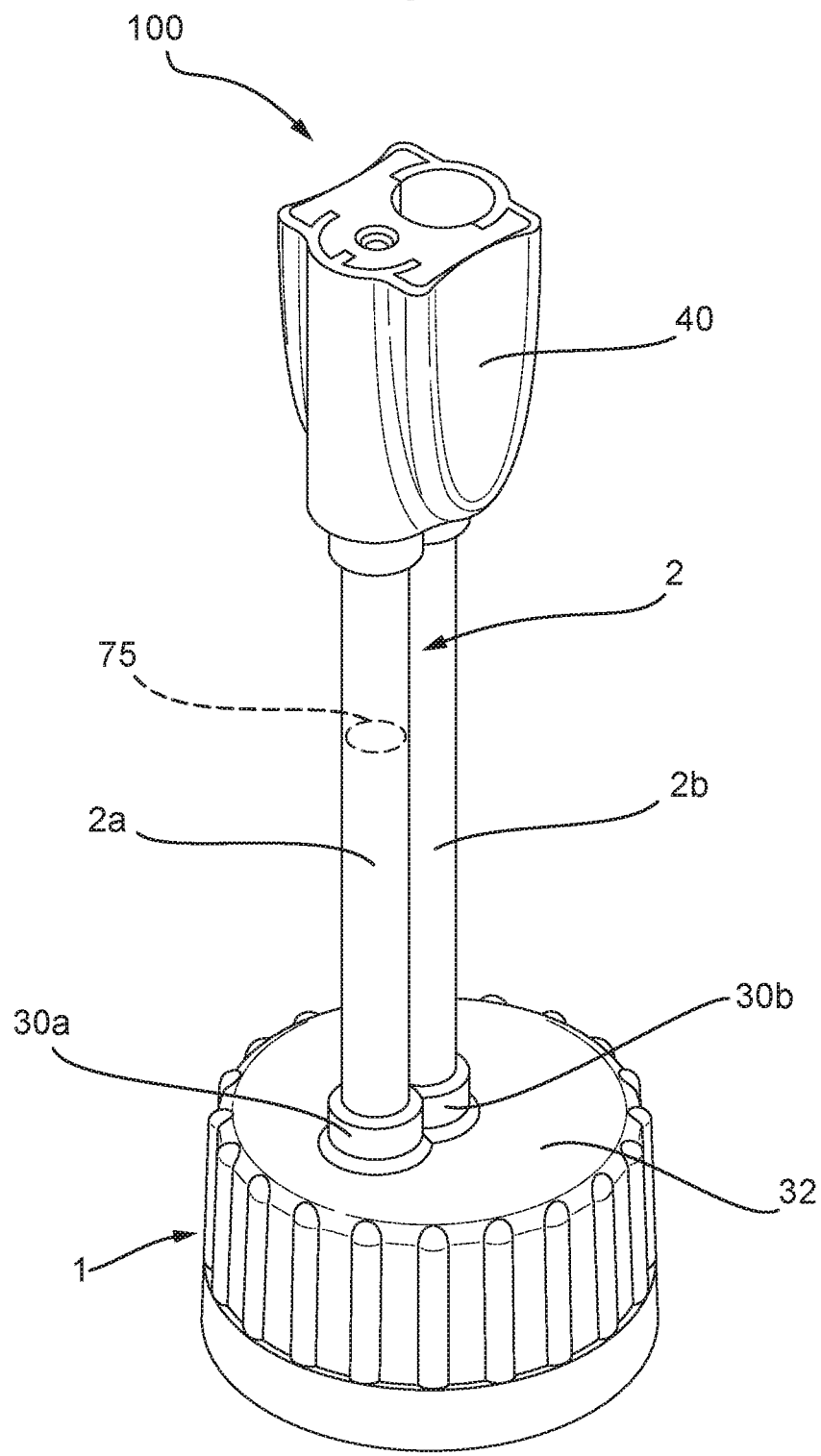
FIG. 7 is a perspective view of a water bottle cap assembly of a seventh embodiment of the present invention.

FIG. 7 shows another embodiment of the present invention. This embodiment is the same as the embodiment shown in FIG. 1a except in that a second separator 75 is located in a fluid pathway connected to the inlet (preferably, as shown, in the first tubular member 2a connected to the inlet 31 via the first inner conduit 20a). It should be noted that the remaining features of the embodiment in FIG. 7 are exactly the same as those of the embodiment in FIG. 1a. In another embodiment, the second separator 7 is provided as in FIG. 7 and the first separator 7 (and associated seals 4,5 and connector 3) is omitted.

The skilled person will appreciated that the water bottle cap 1 described herein, conversely to the prior art apparatus, will allow room air to be filtered before exposure to water in the water bottle.

The present invention will also support the use of either air insufflation or $CO_2$ without the need for a dedicated bottle to one or the other.

Furthermore, the present invention will allow using separating means (separators 7,75) to separate liquid or solid particles not only from the incoming room air flow but also from any incoming gas (e.g., $CO_2$) entering the water bottle. This will prevent contaminants from entering the water bottle.

Moreover, given separating means are enclosed and safely located in, for example, the cap 1, no additional enclosures are needed to protect the separating means.

In light of the above the apparatus of the present invention is more easily manufactured, robust and cost-effective than conventional prior art apparatus. In addition, the water bottle cap 1 will have the advantage of being re-usable with minimal risk of cross contamination.

The present invention is not limited to the specific embodiments described above and it will be understood that features disclosed as part of one embodiment can, if appropriate, be used in combination with other embodiments. Alternative arrangements and suitable materials will be apparent to a reader skilled in the art.

Figure 8:
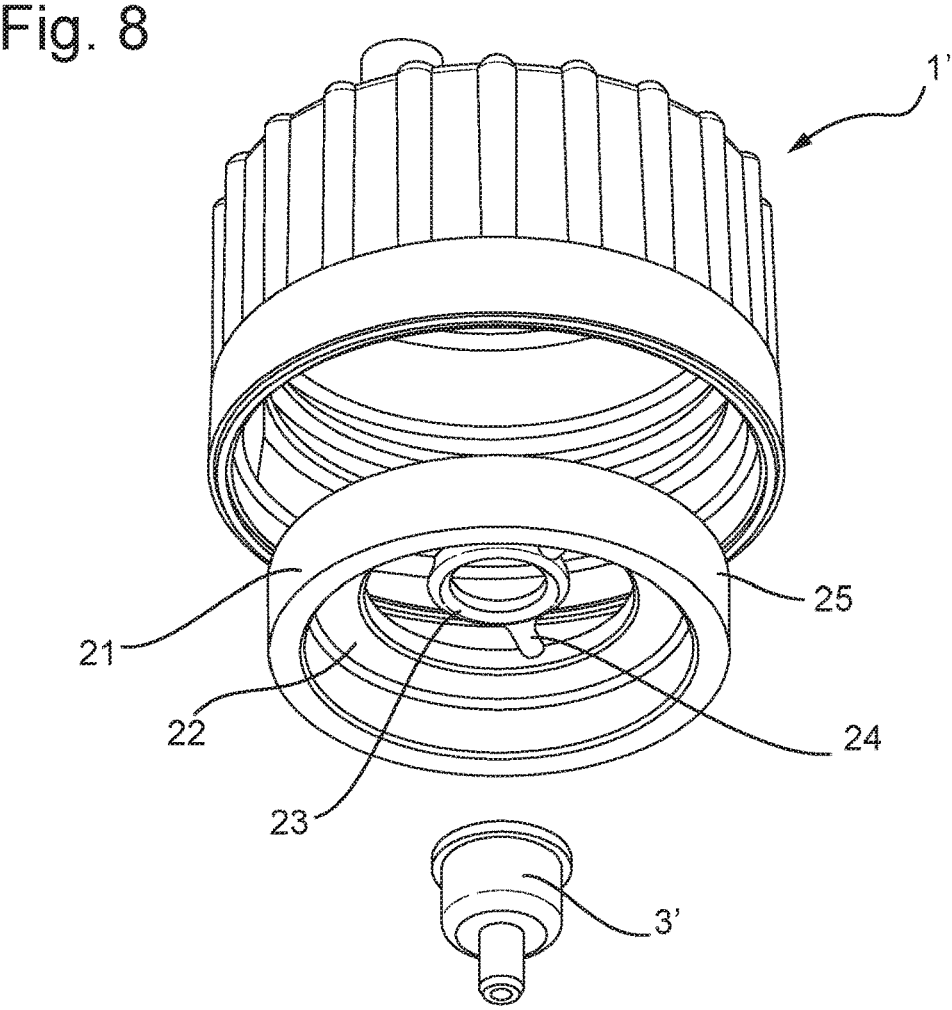
FIG. 8 is a perspective view of a water bottle cap assembly of an eighth embodiment of the present invention, and specifically comprising a single-piece seal element.

For example, FIG. 8 shows a water bottle cap 1' of an endoscope system. The remaining components of the endoscope system, such as the water bottle itself, the endoscope camera, and the fluid tubes connected to the water bottle cap and extending to the camera, are not shown but it will be readily apparent to the skilled person how these components are provided in an endoscope system.

The water bottle cap 1' is provided with a seal member 25. The seal member 25 is a single piece seal element and has a radially inner seal 23 and a radially outer seal 22 that are joined together by three radial straight spokes 24 arranged circumferentially equidistant from each other. The radially inner seal 23 and the radially outer seal 22 of FIG. 8 are substantially circular and annular in shape, but other shapes and/or configurations may be adopted. It will be appreciated that a different number of spokes (including at least one spoke) as well as different arrangements and/or designs (e.g., curved or inclined spokes) can be used. It will be also appreciated that such an integrally formed one-piece seal element can be easily and efficiently assembled in, or disassembled from, the cap 1'.

Figure 10:
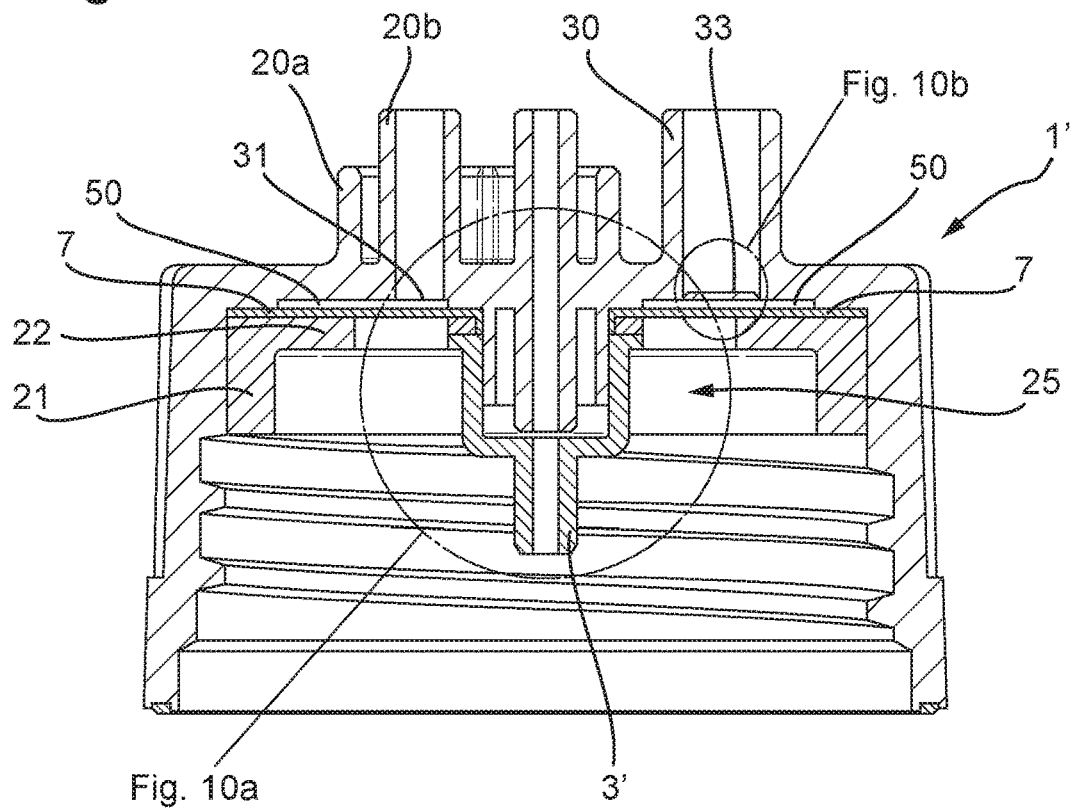
FIG. 10 is a side view of the water bottle cap assembly shown in FIG. 8.

The seal element 25 is of a resiliently and elastically deformable material. The seal element 25 has a radially outer seal 22 having an L-shaped cross-section—two sealing portions 21,22 are shown in FIG. 8 and FIG. 10 intersecting one another to form an L-shape in cross-section. One portion 22 has an annular planar shape and abuts the separator 7, and the other portion 21 has a cylindrical shape and abuts the side walls of the cap 1'. The seal 25 is held adjacent the internal upper surface of the cap (with the separator 7 sandwiched therebetween) by means of a push/interference fit connection with the internal walls of the cap 1'.

A connector 3' retains the radially inner seal 23 adjacent the inner surface of the cap wall by a push/interference press/fit connection, instead of a screw thread connection as in previously described embodiments. This allows the radially inner seal 23 (and hence the separating means 7) to be easily and efficiently secured and/or removed from the central part of the cap, through which the outlet 70 extends. It will be appreciated that other means can be used to hold the inner seal 23 including but not limited to snap clip means.

In use, when the cap 1' is screw threadedly engaged with the opening of the water bottle, the bottle opening abuts the seal 25 and presses/clamps the seal portion 22 against the internal upper wall of the cap. In this way, the seal portion 22 provides support for the radially outermost perimeter of separator 7 and reduces the possibility of incoming gas (for example, air) leaking past the separator 7 at said perimeter. The other seal portion 21 has a cylindrical shape which is sized so as to compliment the cap side walls press against the interior of the cap side walls, and this further reduces the possibility of incoming air leaking past the separator 7 at said perimeter.

Figure 10A:
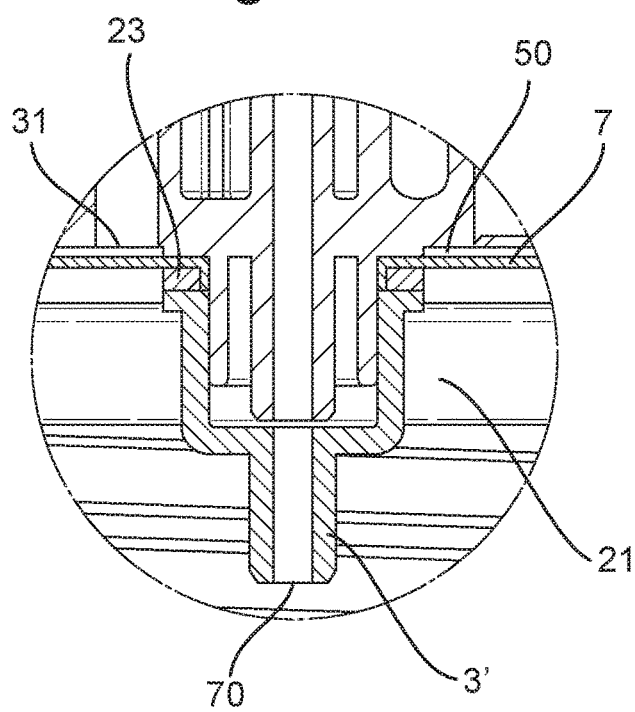
FIG. 10a is an enlarged view of the detail C shown in FIG. 10.

The central inner part of the separator 7 is similarly held in place by the radially inner seal 23 which abuts the separator 7 as shown in FIG. 10 and FIG. 10a. The inner seal 23 is held adjacent the inner surface of the cap wall (with the separator 7 sandwiched therebetween) by means of an push/interference fit with the second inner conduit 20b of the outlet 70 through which the water flows out from the water bottle in use. When the connector 3' engages the second inner conduit 20b, the connector 3' abuts the central seal 23 and presses/clamps the inner seal 23 against the internal upper wall of the container/cap. In this way, the inner seal 23 provides support for the radially innermost perimeter of the separator 7 and reduces the possibility of incoming air leaking past the separator 7 at said perimeter. The inner seal 23 also expands radially inwardly so as to press against the second inner conduit 20b, and this further reduces the possibility of incoming air leaking past the separator 7 at said perimeter.

Each spoke 24 abuts the separating means so as to provide support thereto. In this way, as gas (for example, air) flows through the separator 7, each spoke 24 assists in preventing the separator from being moved or deflected in the direction of the gas flow by the gas. The or each spoke 24 may be resiliently sprung biased towards the separator 7 so as to press against the separator 7. This may be achieved by configuring the seal member 25 so that, when in a relaxed state, each spoke 24 arches out of the plane in which the inner and outer seals 23,22 are located. In this way, when the seal member 25 is located in the cap 1', each spoke 24 presses against the separator 7 and tends to be deflected by the separator 7 against its inherent spring bias and into said plane of the inner and outer seals 23,22.

Figure 9:
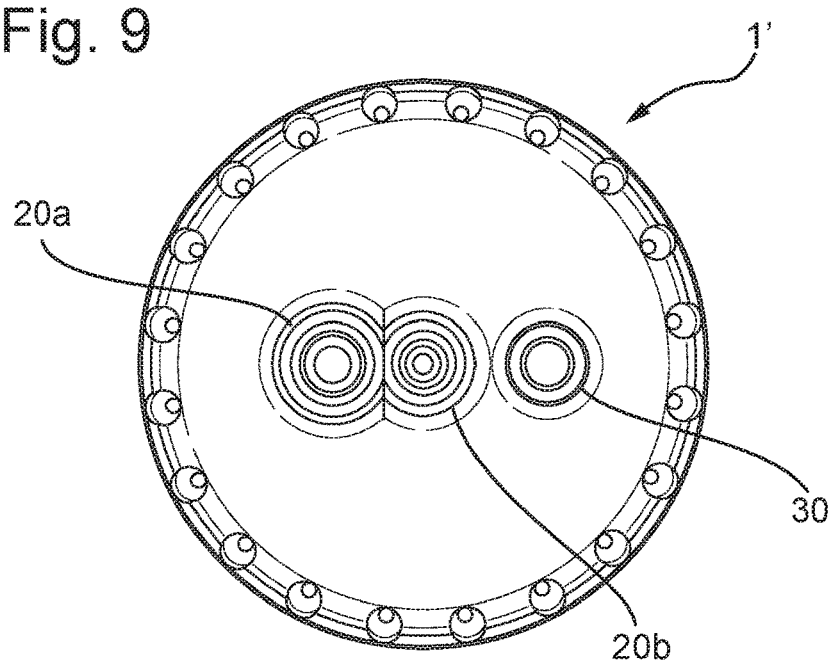
FIG. 9 is a top view of the water bottle cap assembly shown in FIG. 8, comprising an incoming gas (e.g., carbon dioxide, $CO_2$) port.

FIG. 9 and FIG. 10 show that the cap 1' may also comprise an additional or auxiliary port 30 for a secondary gas (for example, carbon dioxide, $CO_2$) supply. As a result, the separator 7 removes liquid or solid particles from the incoming air entering the water bottle through the inlet 31 of the first inner conduit 20a, and/or from an incoming secondary gas (carbon dioxide, $CO_2$) supply entering the water bottle through an inlet 33 provided by the port 30.

As for the previously described embodiments, the water bottle cap 1' has a recess 50 which is arranged between the inlets 31,33 on one side, and the separator 7 on the other side of the recess. The recess 50 is preferably defined about 0.2 mm deep into the internal upper wall of the cap/container, but other suitable depths can be adopted. The recess 50 thereby spaces the inlets 31,33 from the separator 7. The inlet 31 opens into the recess 50 and so incoming air flows from the first inner conduit 20a into a cavity defined between the recess 50 and the separator 7. Equally, the inlet 33 opens into the recess 50, and so incoming gas (e.g., $CO_2$) flows from the inner conduit of the port 30 into a cavity defined between the recess 50 and the separator 7. It will be appreciated that the seal member 25 can be configured in the cap so as to maximise the cross-sectional area of a fluid flow path in the direction of the flow between the inlets 31,33 and the separator 7. As a result, a reduction of mass flow rate of the incoming air/gas, caused by the flow resistance of a separator, can be partially or wholly compensated or mitigated, therefore improving separating/filtering of the air and/or external gas entering the container.

Figure 10B:
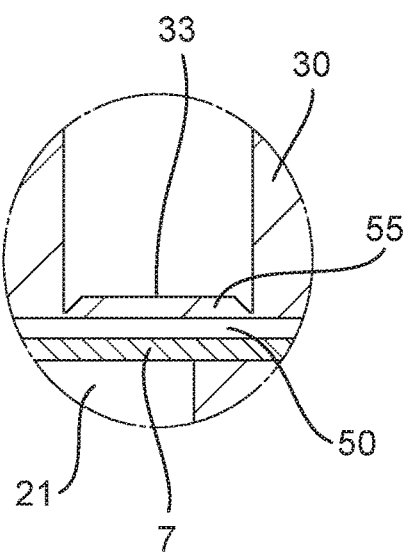
FIG. 10b is an enlarged view of the detail B shown in FIG. 10.

FIG. 10 and FIG. 10b also show a frangible line forming a closed loop about a portion 55 of the cap 1'. The frangible line (for example, in the form of a line of reduced material thickness) can be selectively broken and said portion 55 subsequently removed so as to provide the auxiliary port 30 between the interior and exterior of the container. In this way, a cap 1' can be provided with just one inlet and one outlet, but with the capability of being conveniently provided with a second inlet 33 at the option of the user.

The invention claimed is:

1. An endoscope water bottle cap for an endoscopic device, the water bottle cap comprising:
    an inlet through which, in use, a gas flows into a water bottle associated with the cap;
    an outlet through which, in use, water flows out of the water bottle to the endoscopic device; and
    separating means arranged to separate at least one of liquid and solid particles from the gas that enters the water bottle,
    wherein the separating means is retained on an internal surface of an upper wall of the water bottle cap by a securing means.

2. The water bottle cap according to claim 1, wherein the separating means has an annular shape.

3. The water bottle cap according to claim 1, wherein the separating means is located adjacent an upper wall of the water bottle cap.

4. The water bottle cap according to claim 1, wherein the separating means is arranged on an internal surface of an upper wall of the water bottle cap.

5. The water bottle cap according to claim 1, wherein the securing means comprises a sealing member.

6. The water bottle cap according to claim 5, wherein the sealing member comprises an inner sealing member and a perimeter sealing member.

7. The water bottle cap according to claim 6, wherein the inner sealing member is discrete from the perimeter sealing member.

8. The water bottle cap according to claim 6, wherein the inner sealing member and the perimeter sealing member are connected to one another by at least one radially extending spoke, to integrally form a one-piece single sealing member.

9. The water bottle cap according to claim 6, wherein the inner sealing member and the perimeter sealing member are connected to one another by a plurality of radially extending spokes circumferentially spaced equidistant from each other.

10. The water bottle cap according to claim 9, wherein each of the spokes abuts the separating means so as to provide support to the separating means.

11. The water bottle cap according to claim 9, wherein each of the spokes is resiliently spring biased towards the separating means so as to press against the separating means.

12. The water bottle cap according to claim 6, wherein the inner sealing member abuts a radially inner annular region of the separating means, and the perimeter sealing member abuts a radially outer annular region of the separating means, to thereby retain the separating means in position.

13. The water bottle cap according to claim 5, wherein the sealing member is made of a resiliently deformable material.

14. The water bottle cap according to claim 5, wherein the securing means comprises a connector which is secured to the internal surface of the upper wall of the water bottle cap by a selected one of the group consisting of screw thread means, push/interference fit means and snap-clip means.

15. The water bottle cap according to claim 1, wherein the separating means is arranged between the upper wall of the water bottle cap and the securing means.

16. The water bottle cap according to claim 1, wherein the separating means is arranged between the inlet and the securing means.

17. The water bottle cap according to claim 1, wherein a cavity is provided between the upper wall of the water bottle cap and the separating means, and wherein the inlet opens in to said cavity.

18. The water bottle cap according to claim 1, further comprising a conduit in which said outlet is provided, the conduit extending through the separating means, from one side of the separating means to an opposite side.

19. The water bottle cap according to claim 1, wherein the separating means is a filter.

20. The water bottle cap according to claim 19, wherein the filter is made of porous material.

21. The water bottle cap according to claim 19, wherein the filter is made of a resiliently deformable material.

* * * * *